(12) United States Patent
Lee et al.

(10) Patent No.: US 9,741,536 B2
(45) Date of Patent: Aug. 22, 2017

(54) HIGH ASPECT RATIO STRUCTURE ANALYSIS

(71) Applicant: FEI Company, Hillsboro, OR (US)

(72) Inventors: Sang Hoon Lee, Hillsboro, OR (US);
Stacey Stone, Portland, OR (US);
Jeffrey Blackwood, Portland, OR (US);
Michael Schmidt, Gresham, OR (US)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/433,354

(22) PCT Filed: Oct. 4, 2013

(86) PCT No.: PCT/US2013/063479
§ 371 (c)(1),
(2) Date: Apr. 2, 2015

(87) PCT Pub. No.: WO2014/055876
PCT Pub. Date: Apr. 10, 2014

(65) Prior Publication Data
US 2015/0243478 A1    Aug. 27, 2015

Related U.S. Application Data

(60) Provisional application No. 61/710,580, filed on Oct. 5, 2012.

(51) Int. Cl.
*G01R 23/02* (2006.01)
*H01J 37/305* (2006.01)
(Continued)

(52) U.S. Cl.
CPC .......... *H01J 37/3053* (2013.01); *C23C 14/46* (2013.01); *H01J 37/28* (2013.01);
(Continued)

(58) Field of Classification Search
CPC .... H01J 37/3053; H01J 37/28; H01J 37/3056; H01J 37/3178; H01J 2237/3174;
(Continued)

(56) References Cited

U.S. PATENT DOCUMENTS 4,460,434 A * 7/1984 Johnson ............ H01L 21/31055
204/192.34
5,435,850 A    7/1995 Rasmussen
(Continued)

FOREIGN PATENT DOCUMENTS

CN    1979791    6/2007
CN    101153855    4/2008
(Continued)

*Primary Examiner* — John Brayton
(74) *Attorney, Agent, or Firm* — Scheinberg & Associates, P.C.; Michael O. Scheinberg; John E. Hillert

(57) ABSTRACT

Curtaining artifacts on high aspect ratio features are reduced by reducing the distance between a protective layer and feature of interest. For example, the ion beam can mill at an angle to the work piece surface to create a sloped surface. A protective layer is deposited onto the sloped surface, and the ion beam mills through the protective layer to expose the feature of interest for analysis. The sloped mill positions the protective layer close to the feature of interest to reduce curtaining.

25 Claims, 8 Drawing Sheets

(51) Int. Cl.
  *H01J 37/28* (2006.01)
  *H01J 37/317* (2006.01)
  *C23C 14/46* (2006.01)
  *G01N 1/32* (2006.01)

(52) U.S. Cl.
  CPC ...... *H01J 37/3056* (2013.01); *H01J 37/3178* (2013.01); *G01N 1/32* (2013.01); *H01J 2237/3174* (2013.01); *H01J 2237/31745* (2013.01); *H01J 2237/31749* (2013.01)

(58) Field of Classification Search
  CPC .. H01J 2237/31745; H01J 2237/31749; C23C 14/46; G01N 1/32
  See application file for complete search history.

(56) References Cited

U.S. PATENT DOCUMENTS

| | | | |
|---|---|---|---|
| 5,851,413 A | 12/1998 | Casella et al. | |
| 6,127,277 A * | 10/2000 | DeOrnellas | H01J 37/32165 156/345.28 |
| 6,517,734 B1 | 2/2003 | Muller et al. | |
| 7,858,936 B2 | 12/2010 | Bray et al. | |
| 8,822,921 B2 | 9/2014 | Schmidt et al. | |
| 8,859,963 B2 | 10/2014 | Moriarty et al. | |
| 8,859,998 B2 | 10/2014 | Blackwood et al. | |
| 8,912,490 B2 | 12/2014 | Kelley et al. | |
| 2001/0003035 A1 | 6/2001 | Ozarski et al. | |
| 2002/0079463 A1 | 6/2002 | Shichi et al. | |
| 2003/0201249 A1 | 10/2003 | Harker et al. | |
| 2006/0226376 A1 | 10/2006 | Fujii | |
| 2007/0087572 A1* | 4/2007 | Le Roy | H01J 37/3005 438/712 |
| 2008/0314871 A1* | 12/2008 | Toth | B81C 1/00531 216/48 |
| 2009/0205092 A1 | 8/2009 | Wang et al. | |
| 2011/0031388 A1* | 2/2011 | Bower | H01J 37/244 250/281 |
| 2012/0235055 A1 | 9/2012 | Madokoro et al. | |
| 2013/0143412 A1* | 6/2013 | Moriarty | G01N 1/286 438/759 |
| 2013/0186747 A1 | 7/2013 | Schmidt et al. | |
| 2013/0248354 A1 | 9/2013 | Keady et al. | |
| 2013/0328246 A1 | 12/2013 | Wells et al. | |
| 2015/0243477 A1 | 8/2015 | Stone et al. | |
| 2015/0243478 A1 | 8/2015 | Lee et al. | |

FOREIGN PATENT DOCUMENTS

| | | |
|---|---|---|
| EP | 2068160 A2 | 6/2009 |
| WO | 2014106200 | 7/2014 |
| WO | 2014106202 | 7/2014 |

* cited by examiner

HIGH ASPECT RATIO STRUCTURE ANALYSIS

TECHNICAL FIELD OF THE INVENTION

The present invention relates to charged particle beam processing of structures.

BACKGROUND OF THE INVENTION

A common method of examining microscopic (including nanometer scale) structures for process monitoring and failure analysis is to cut a trench in the structure with a focused ion beam (FIB) to expose a cross section, and then view the cross section with a scanning electron microscope (SEM). Ion beam milling artifacts, however, can distort the exposed cross section so that the electron beam image does not show an accurate image of the structure.

One artifact is referred to as "curtaining," because it can look like a curtain. Curtaining occurs when different materials are removed at different rates, such as when the sample is composed of materials that are milled at different rates by the ion beam. Curtaining can also occur when milling a surface that has an irregular shape.

Severe artifacts can be created when exposing a feature having a height that is much greater than its width. Such a structure is referred to as a "high aspect ratio" feature. For example, a feature having a height four times greater than its width would be considered a high aspect ratio feature. For example, holes or contacts between layers in an integrated circuit often have a height that is several times greater than its width.

As semiconductor fabrication processes pack more circuitry into smaller packages, integrated circuit designs are becoming more three-dimensional (3D) and incorporate more high aspect ratio features. In analyzing high aspect ratio structures, especially unfilled contact holes, for 3D integrated circuit (IC) structures such as 3D NAND circuits, conventional ion beam sample preparation causes unacceptable artifacts, such as structure distortion and curtaining.

When there are unfilled high aspect ratio holes on a sample, there are large differences in the milling rates between the solid regions and the regions adjacent to the unfilled hole. The large difference in milling rates results in curtaining or waterfall effects, another artifact that distorts the shape of the hole. Structural damage and artifacts from the ion beam milling process make it difficult to analyze high aspect ratio vertical structures.

For example, one structural feature that process engineers need to observe is a through-silicon via (TSV). Cross-sectioning TSVs is a common practice in semiconductor labs to characterize voids and surface interfaces. Due to the depth of TSVs, typically 50-300 nm, milling a cross section of a TSV with an ion beam can result in substantial curtaining.

Because of the damage and artifacts caused by the use of ion beam milling to expose features, the images do not faithfully show the results of the fabrication process. The artifacts interfere with measurements and with an assessment of the fabrication process because the image and measurements show the results of the sample preparation and not just a product of the manufacturing process.

A method for viewing and measuring high aspect ratio structures without altering the structures or creating artifacts is needed.

SUMMARY OF THE INVENTION

An object of the invention is to provide a reliable system for analyzing high aspect ratio structures.

A sloped trench is milled into a work piece surface. A protective layer is deposited on a surface of the sloped trench, and then a cross section of the feature of interest is exposed by milling through the protective layer. Artifacts are reduced because the depth of the feature of interest below the protective layer is reduced compared to the depth of the feature below the original work piece surface.

The exposed cross section can be viewed or analyzed using a variety of techniques, such as scanning electron microscopy, optical microscopy, x-ray analysis, or micro Raman analysis. The process provides reliable analysis results for the high aspect ratio 3D IC structure process and other high aspect ratio processes including holes, trenches, and other structures.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Embodiments of the invention reduce the damage and artifacts in features exposed by ion beam milling. Embodiments are particularly useful for analysis of new 3D structures, such as 3D NAND structures, which include unfilled high aspect ratio holes. The process can be performed on a sample in the form of a wafer or on a smaller sample, such as an individual integrated circuit.

One embodiment of the present invention mills the sample at a non-vertical angle prior to deposition of a protective layer, followed by vertical milling to expose a cross section of a high aspect structure for imaging. By adjusting the tilt stage angle and the position of the vertical mill, a ROI can be exposed at any desired depth of high aspect ratio structure.

By tilting the stage, for example, between about 30° to about 33.5° prior to deposition of a protective layer, curtain effects are reduced or eliminated as material between the protective layer and the ROI is reduced, and the depth of the ROI below the surface is shortened. The shorter depth below the surface with the protective layer reduces curtaining, as there is less material above the ROI to obstruct the ion beam non-uniformly.

Because of the angle at which the cross section is cut, the alternating solid material and voids in the exposed cross section face exhibits steps of about 1 µm to 1.5 µm in height. A preferred protective layer deposition process covers the steps, if present in the sample, to present a relatively uniform surface for the ion beam to mill. For example, the electron-beam-induced deposition is performed using a relatively high voltage electron beam, preferably greater than 10 keV, greater than 20 keV, and more preferably about 30 keV. This enables filling the steps created by empty high-aspect-ratio structures with protection materials such as platinum or tungsten. Consequentially, the invention provides reliable ROI analysis with this robust solution. Other deposition techniques can be used, such as other beam-induced deposition, including ion beam-induced deposition, laser beam-induced deposition, or cluster beam deposition.

Figure 1:
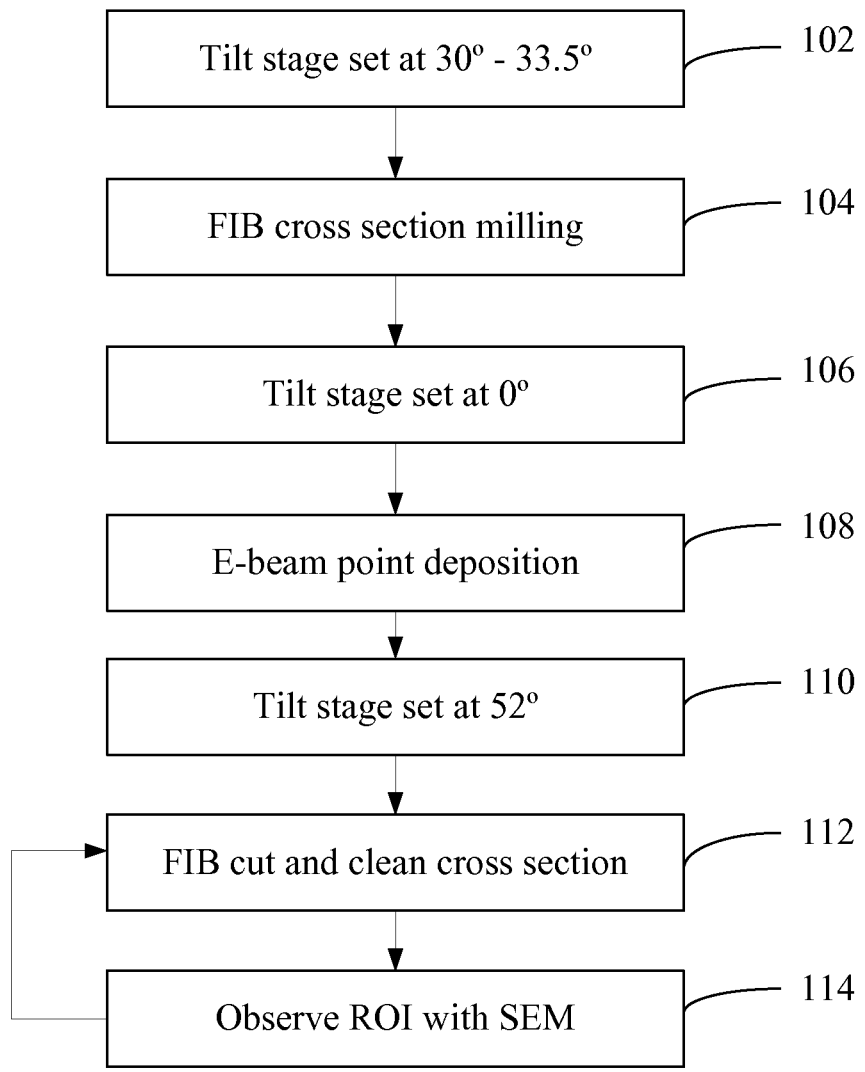
FIG. 1 is a flow chart showing the process steps as illustrated in FIGS. 2-5.
Figure 7:
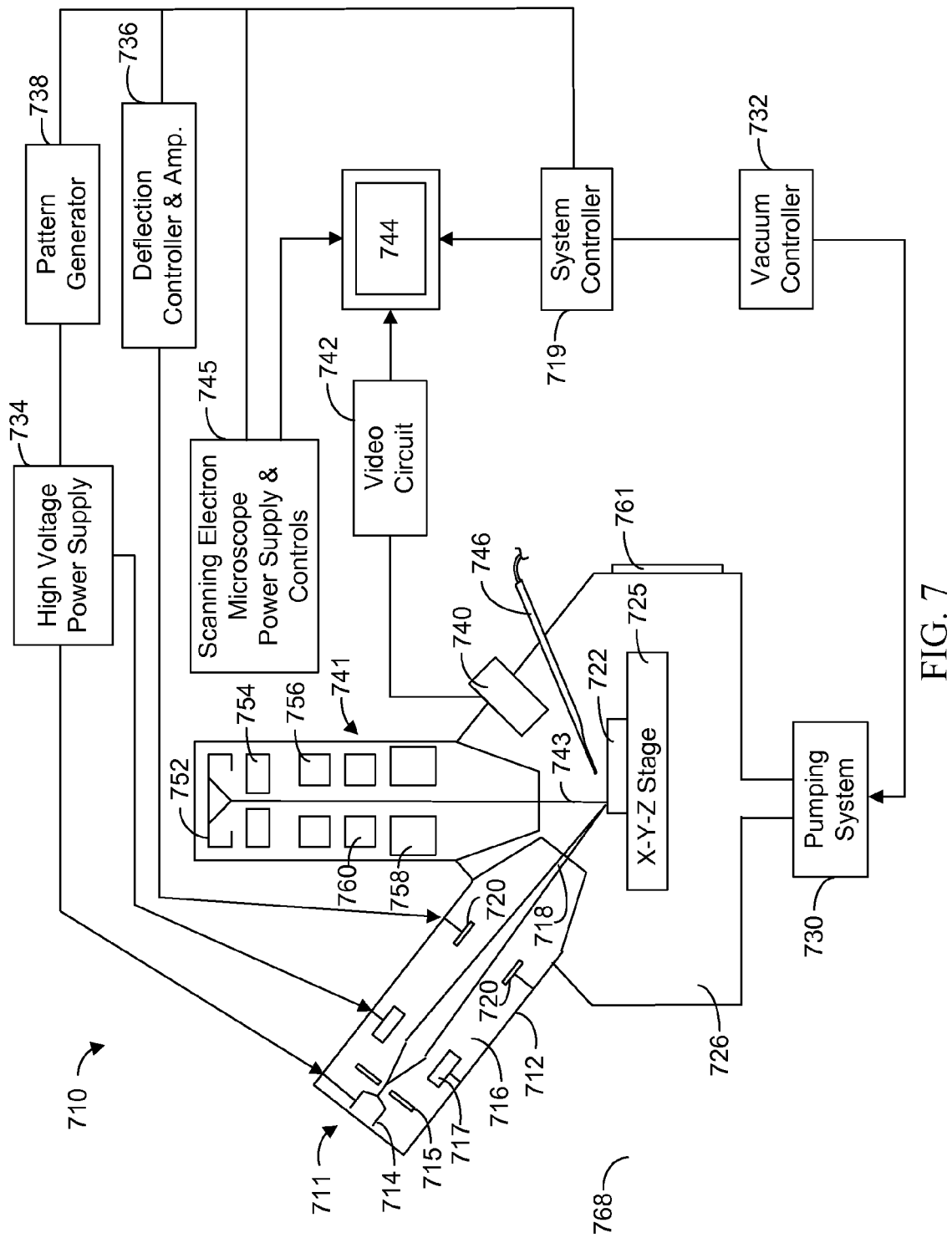
FIG. 7 shows schematically a dual beam system that can be used to implement the present invention.

FIG. 1 is a process flow chart showing the steps of a process that provides a method of ion beam analysis for the high aspect ratio structure analysis of a 3D integrated circuit. FIGS. 2-5 show, not to scale, the sample during the process steps, and FIG. 7 shows a typical dual beam system that can be used to perform process of FIG. 1. The process of FIG. 1 is described as being performed on a dual beam system in which the electron column is vertical and the ion column is tilted at 52°. In other hardware configurations, the stage tilts will be different to produce the same relative angles between the beam and the work piece.

Figure 2:
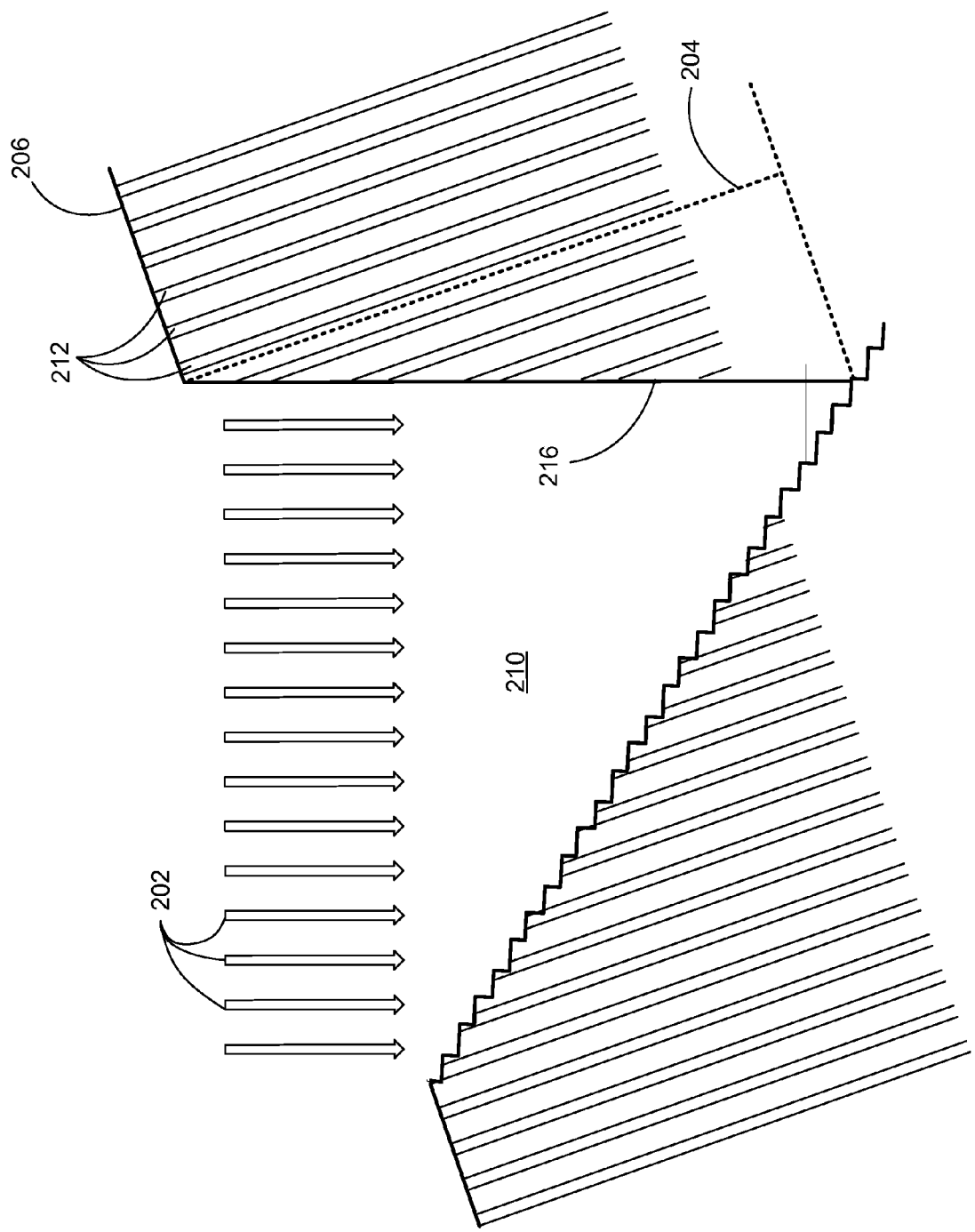
FIG. 2 shows a tilted sample being cross-section milled with a FIB.

In step 102, the stage is tilted to an angle of between about 30° and about 33.5°, resulting in an angle of between about 18.5° and about 22° between the ion beam 202 and a normal 204 to the work piece surface 206. In other embodiments, the angle between ion beam 202 and normal 204 is between 5° and 50°. In step 104, the FIB mills a trench 210 to expose a cross section face 216 as shown in FIG. 2 that includes high aspect ratio holes 212. The cross section face 216 is not normal to the sample surface. Each arrow shows a scan path of ion beam 202, which scan goes into the plane of the page as the beam scans to mill the trench.

Because fewer secondary electrons escape from the bottom of a narrow trench, the trench 210 is preferably sufficiently wide to provide a good secondary electron signal for imaging from ROIs deep in the trench. The wide cross sectional area permits the secondary electrons to escape from the bottom of the trench to be detected. Typically, the cross section of the trench area should be at least twice the size of the region of interest.

Figure 3:
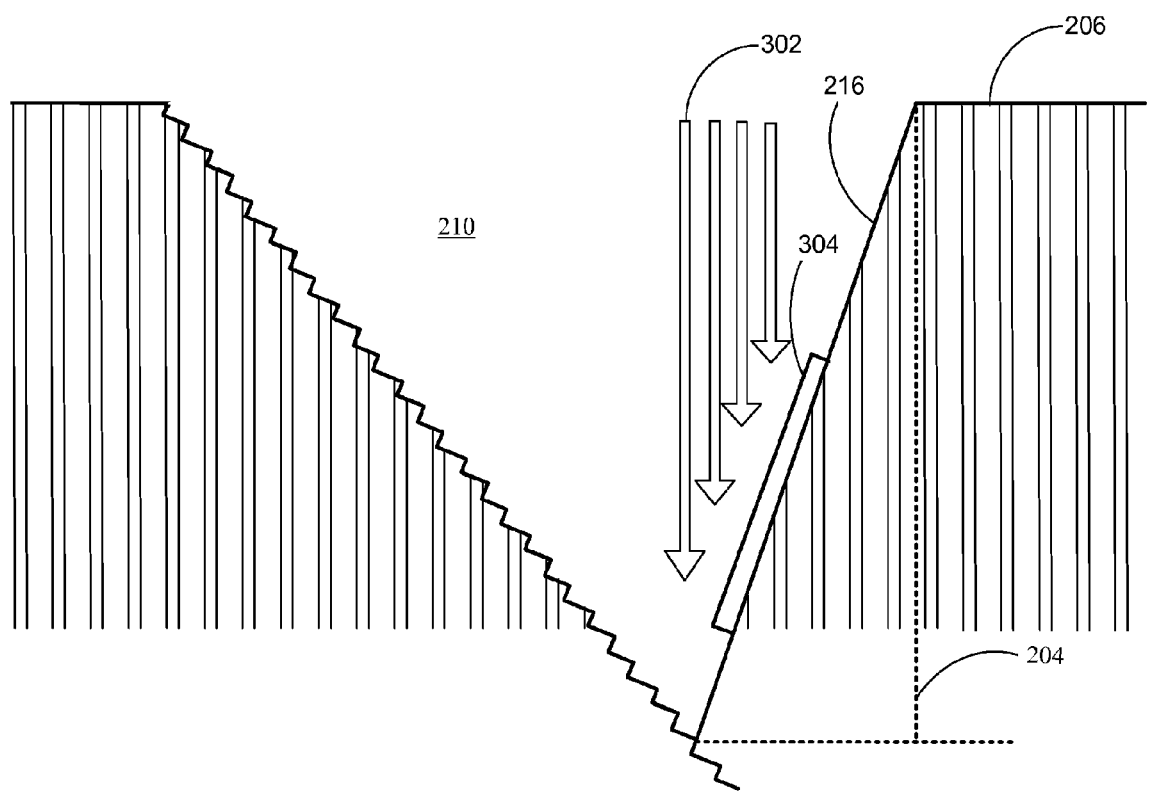
FIG. 3 shows an un-tilted sample undergoing e-beam point deposition.

In step 106, the stage is tilted stage to 0° so that an electron beam 302 is oriented normal to the work piece surface 206 and between 18.5° and 22° to the sloped surface 216. In step 108, a protective layer 304 of platinum, tungsten, or other material is deposited above the region of interest using electron beam-induced deposition as shown in FIG. 3. An electron energy of about 30 keV is preferably used for the best step coverage by increasing the momentum of the electrons to fill in the exposed steps.

Figure 4:
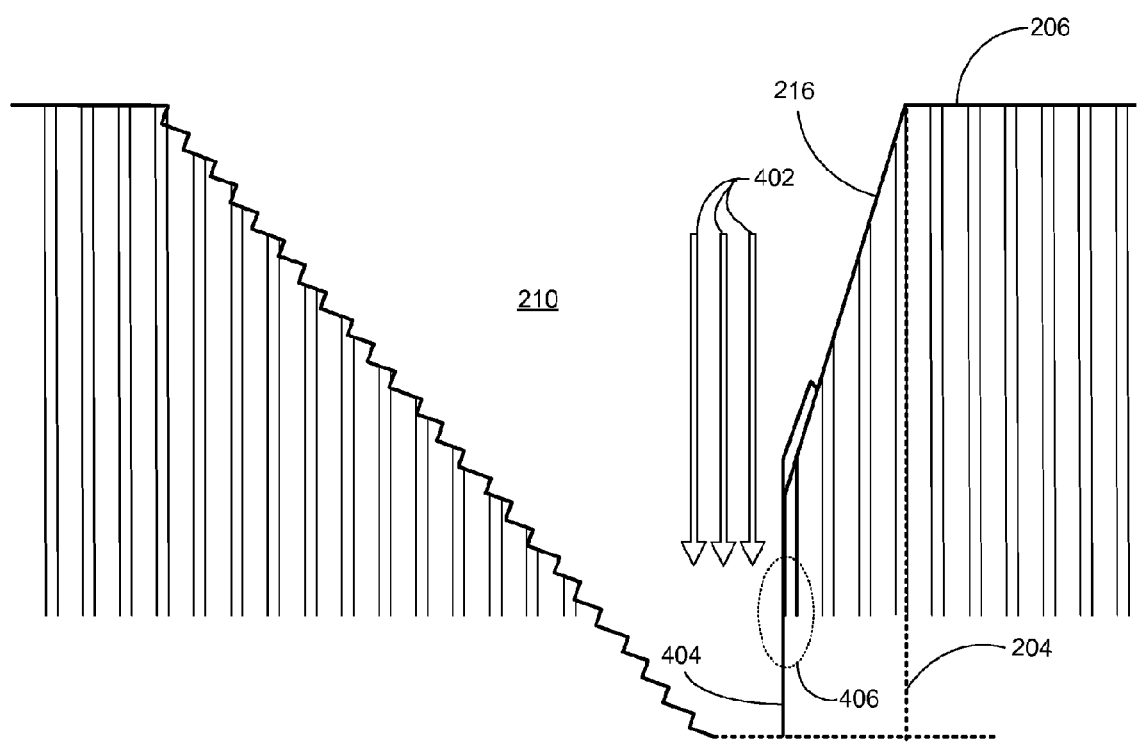
FIG. 4 shows a tilted sample with a FIB-milled cross-section.

Step 110 shows the stage is tilted to 52° so that the ion beam is normal to the surface as shown in FIG. 4. Step 112 shows a FIB cross section is performed. A 52° stage tilt makes a perpendicular angle between sample surface and ion column.

Figure 5:
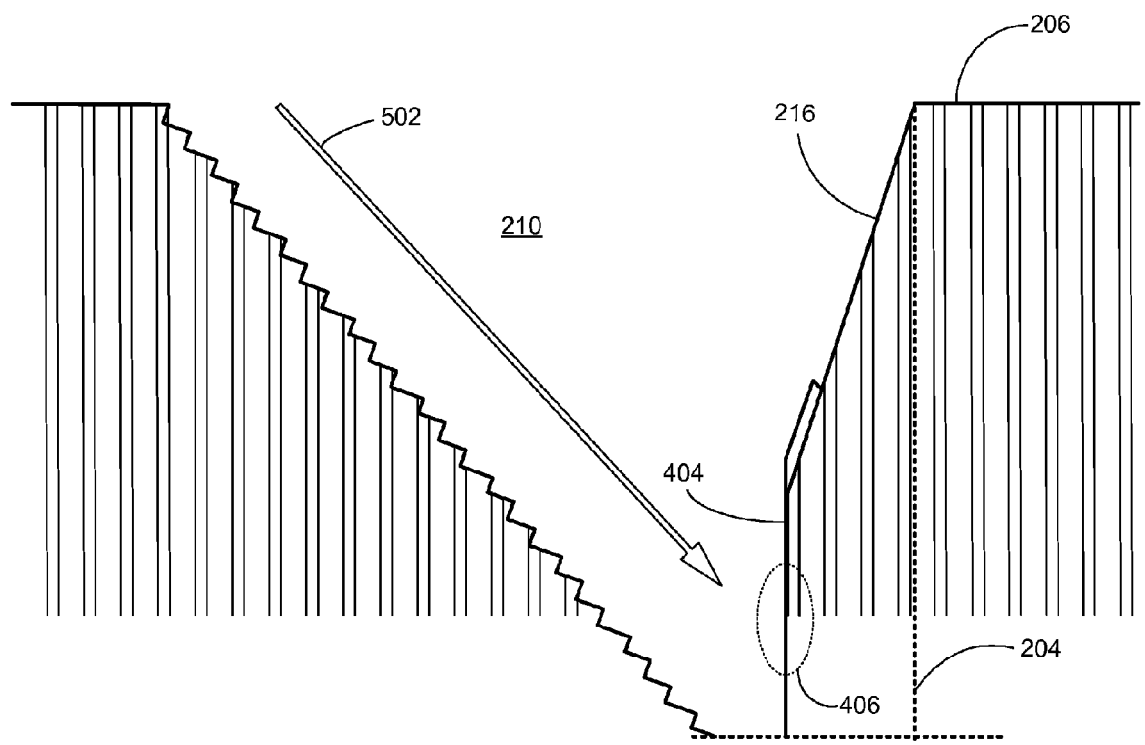
FIG. 5 shows a slice and view process using SEM imaging on a region of interest (ROI)

Step 112 forms a vertical cross section of the region of interest that can be imaged or analyzed by a variety of methods, including scanning electron microscopy, x-ray analysis, micro-Raman, or other methods. FIG. 4 shows the ion beam 402 makes a vertical cut to expose a vertical surface 404 through the region of interest 406. The ion beam 402 processing preferably includes a bulk cut to remove material to form the vertical wall and a cleaning cross section, which removes little material but produces a cleaner surface for observation. Work piece surface 206 represents a first surface, sloped surface 216 represents a second surface, and vertical surface 404 represents a third surface. A portion of the second surface is between the region of interest and the first surface, and the third surface is substantially normal to the first surface. In step 114, the electron beam 502 is directed to the sample to form a scanning electron beam image as shown in FIG. 5.

Optionally, steps 112 and 114 are repeated to continue to step through a feature, to form a series of cross-sectional images so that a 3D representation of a feature in the ROI can be formed. This process is referred to as "slice-and-view," which entails repeatedly removing additional material with the ion beam to expose another face of the ROI and then forming an image of the exposed face using the electron beam.

In prior art cross-sectional processing, in the case of rough surface topology or complex structure in the depth direction, curtain effects are unavoidable as the perpendicular depth is getting more than a few micrometers deeper. By using about a 30° to 33.5° stage tilt angle prior to electron-beam induced deposition, curtain effects are removed as materials above ROI are removed and the depth below surface of the ROI is reduced. At the same time, using high energy electrons covers the steps, which enables partially filling any empty hole of high aspect ratio structure with protection materials such as platinum or tungsten. Consequentially, embodiments provide reliable failure analysis or process monitoring.

By adjusting the stage tilt angle and the position of the ion beam cut to expose the region of interest, an ROI at any depth of high aspect ratio structure can be exposed and examined. It should be understood, of course, that the foregoing relates to exemplary embodiments of the invention and that modifications may be made without departing from the spirit and scope of the invention as set forth in the claims.

Embodiments of the invention shows crisp, clean boundaries between empty channels and the substrate. The robust process allows high aspect ratio structure failure analysis without damage to the structure being investigated.

Figure 6A:
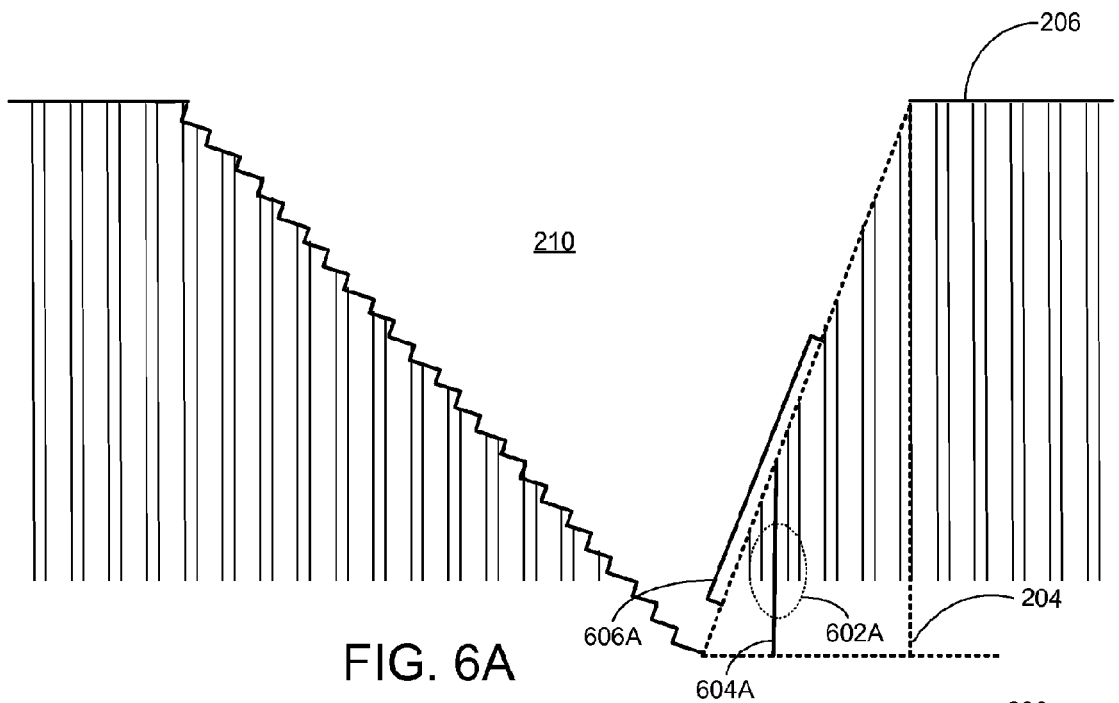
FIGS. 6A-6C show regions of interest at different depths below the work piece surface.
Figure 6B:
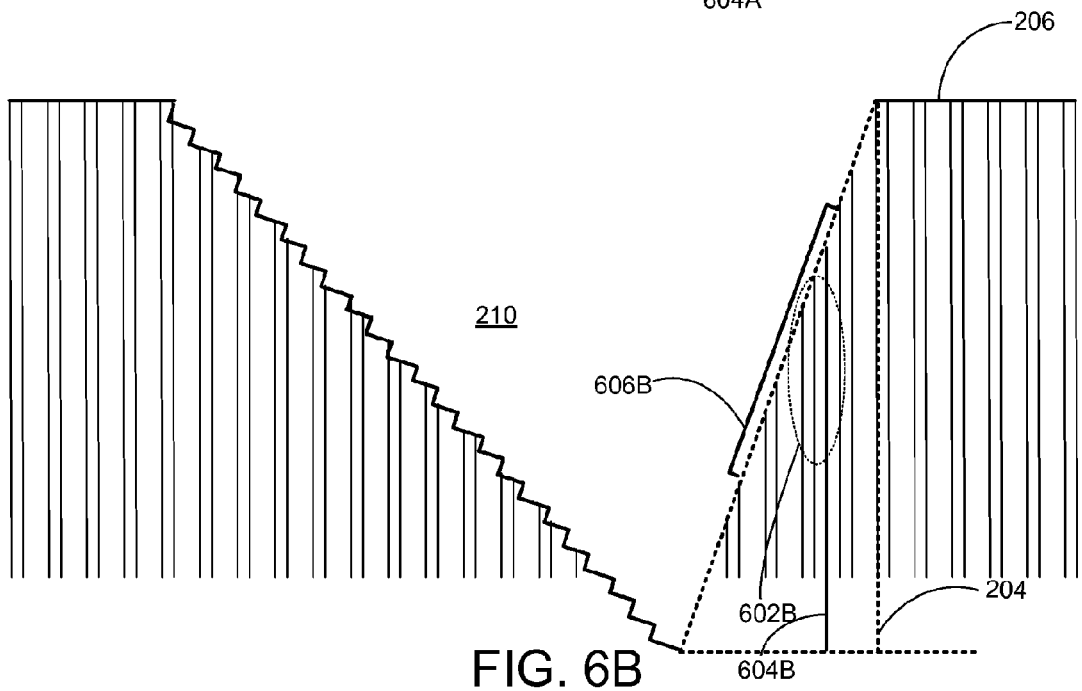
Figure 6C:
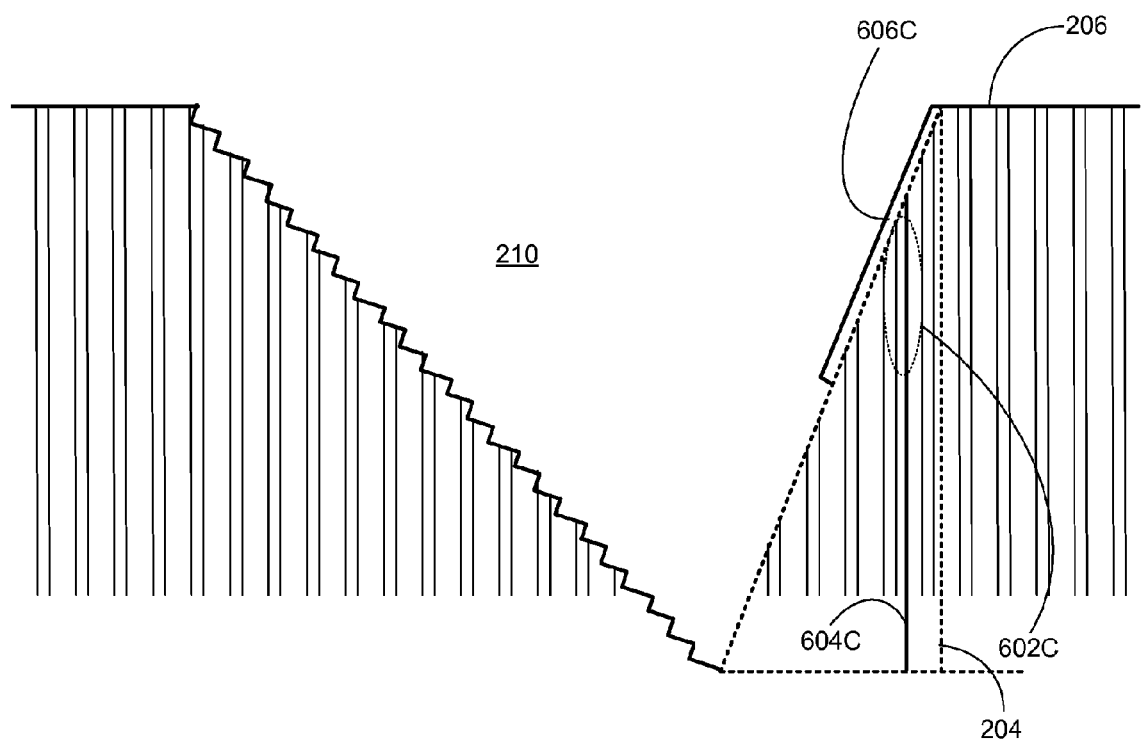

The high aspect ratio feature can be inspected at different depths from the surface by adjusting the angle of face 216 or the position of the vertical cut through face 216. FIGS. 6A, 6B and 6C show regions of interest at different depths below the work piece surface. The samples are shown with the trench 210 milled, but the vertical cut to produce the face for observation is not yet performed. The ovals 602A, 602B, and 602C represent regions of interest, and the vertical lines 604A, 604B, and 604C show the position of the vertical ion beam cut through the electron beam deposited protective layer 606A, 606B, and 606C and through the ROI. The jagged line shows the ion milling as in step 104 above and FIG. 2. The position of the protective layer 606A, 606B, and 606C varies with the position of the ROI. The process for depositing the protective layer preferably fills any holes that are present. In FIG. 6A, the ROI is toward the bottom of the channel hole. In FIG. 6B, the ROI is about ½ way to the bottom of the channel. FIG. 6C shows a ROI toward the top of the channel hole. In FIGS. 6A, 6B, and 6C, the vertical line through the ROI shows the ion beam cut as shown in step 112 through the protective layer. In each case, the distance milled below through the material remaining above the ROI is about the same and is relatively small, so that there is little or no curtaining caused by shading above the ROI.

FIG. 7 shows a typical dual beam system 710 suitable for practicing the present invention, with a vertically mounted SEM column and a FIB column mounted at an angle of approximately 52° from the vertical. Suitable dual beam systems are commercially available, for example, from FEI Company, Hillsboro, Oreg., the assignee of the present application. While an example of suitable hardware is provided below, the invention is not limited to being implemented in any particular type of hardware.

A scanning electron microscope 741, along with power supply and control unit 745, is provided with the dual beam system 710. An electron beam 743 is emitted from a cathode 752 by applying voltage between cathode 752 and an anode 754. Electron beam 743 is focused to a fine spot by means of a condensing lens 756 and an objective lens 758. Electron beam 743 is scanned two-dimensionally on the specimen by means of a deflection coil 760. Operation of condensing lens 756, objective lens 758, and deflection coil 760 is controlled by power supply and control unit 745.

Electron beam 743 can be focused onto substrate 722, which is on movable stage 725 within lower chamber 726. When the electrons in the electron beam strike substrate 722, secondary electrons are emitted. These secondary electrons are detected by a secondary electron detector 740 as discussed below.

Dual beam system 710 also includes focused ion beam (FIB) system 711 which comprises an evacuated chamber having an upper portion 712 within which are located an ion source 714 and a focusing column 716 including extractor electrodes and an electrostatic optical system. The axis of focusing column 716 is tilted 52 degrees from the axis of the electron column. The upper portion 712 includes an ion source 714, an extraction electrode 715, a focusing element 717, deflection elements 720, and a focused ion beam 718. Ion beam 718 passes from ion source 714 through focusing column 716 and between electrostatic deflection means schematically indicated at 720 toward substrate 722, which comprises, for example, a semiconductor device positioned on movable stage 725 within lower chamber 726.

Stage 725 can preferably move in a horizontal plane (X and Y axes) and vertically (Z axis). Stage 725 can also tilt approximately 60° and rotate about the Z axis. A door 761 is opened for inserting substrate 722 onto X-Y stage 725 and also for servicing an internal gas supply reservoir, if one is used. The door is interlocked so that it cannot be opened if the system is under vacuum. Alternatively, an airlock can be used to avoid exposing chamber 726 to atmosphere.

An ion pump (not shown) is employed for evacuating upper portion 712. The chamber 726 is evacuated with turbomolecular and mechanical pumping system 730 under the control of vacuum controller 732. The vacuum system provides within chamber 726 a vacuum of between approximately $1\times10^{-7}$ Torr and $5\times10^{-4}$ Torr. If an etch-assisting gas, an etch-retarding gas, or a deposition precursor gas is used, the chamber background pressure may rise, typically to about $1\times10^{-5}$ Torr.

The high voltage power supply provides an appropriate acceleration voltage to electrodes in ion beam focusing column focusing 716 for energizing and focusing ion beam 718. When it strikes substrate 722, material is sputtered, that is physically ejected, from the sample. Alternatively, ion beam 718 can decompose a precursor gas to deposit a material.

High voltage power supply 734 is connected to liquid metal ion source 714 as well as to appropriate electrodes in ion beam focusing column 716 for forming an approximately 1 keV to 60 keV ion beam 718 and directing the same toward a sample. Deflection controller and amplifier 736, operated in accordance with a prescribed pattern provided by pattern generator 738, is coupled to deflection plates 720 whereby ion beam 718 may be controlled manually or automatically to trace out a corresponding pattern on the upper surface of substrate 722. In some systems the deflection plates are placed before the final lens, as is well known in the art. Beam blanking electrodes (not shown) within ion beam focusing column 716 cause ion beam 718 to impact onto blanking aperture (not shown) instead of substrate 722 when a blanking controller (not shown) applies a blanking voltage to the blanking electrode.

The liquid metal ion source 714 typically provides a metal ion beam of gallium. The source typically is capable of being focused into a sub one-tenth micrometer wide beam at substrate 722 for either modifying the substrate 722 by ion milling, enhanced etch, material deposition, or for the purpose of imaging the substrate 722. Other ion sources, such as a plasma ion source, can also be used.

A charged particle detector 740, such as an Everhart-Thornley detector or multi-channel plate, used for detecting secondary ion or electron emission is connected to a video circuit 742 that supplies drive signals to video monitor 744 and receives deflection signals from controller 719. The location of charged particle detector 740 within lower chamber 726 can vary in different embodiments. For example, a charged particle detector 740 can be coaxial with the ion beam and include a hole for allowing the ion beam to pass. In other embodiments, secondary particles can be collected through a final lens and then diverted off axis for collection.

A gas delivery system 746 extends into lower chamber 726 for introducing and directing a gaseous vapor toward substrate 722. U.S. Pat. No. 5,851,413, to Casella et al. for "Gas Delivery Systems for Particle Beam Processing," assigned to the assignee of the present invention, describes a suitable gas delivery system 746. Another gas delivery system is described in U.S. Pat. No. 5,435,850, to Rasmussen for a "Gas Injection System," also assigned to the assignee of the present invention. For example, a metal organic compound can be delivered to the beam impact point to deposit a metal upon impact of the ion beam or the electron beam. A precursor gas, such as $(CH_3)_3Pt(C_pCH_3)$ to deposit platinum or tungsten hexcarbonyl to deposit tungsten, can be delivered to be decomposed by the electron beam to provide the protective layer in step 108.

A system controller 719 controls the operations of the various parts of dual beam system 710. Through system controller 719, a user can cause ion beam 718 or electron beam 743 to be scanned in a desired manner through commands entered into a conventional user interface (not shown). Alternatively, system controller 719 may control dual beam system 710 in accordance with programmed instructions. A preferred controller is in communication with or includes a memory that stores instructions for automatically carrying out the steps of FIG. 1. In some embodiments, dual beam system 710 incorporates image recognition software, such as software commercially available from Cognex Corporation, Natick, Mass., to automatically identify regions of interest, and then the system can manually or automatically expose cross sections for imaging in accordance with the invention. For example, the system could automatically locate similar features on semiconductor wafers including multiple devices, and expose and form images of features of interest on different (or the same) devices.

The invention has broad applicability and can provide many benefits as described and shown in the examples above. The embodiments will vary greatly depending upon the specific application, and not every embodiment will provide all of the benefits and meet all of the objectives that are achievable by the invention. Particle beam systems suitable for carrying out the present invention are commercially available, for example, from FEI Company, the assignee of the present application.

The present specification discloses both a method and an apparatus for performing the operations of the method. Such apparatus may be specially constructed for the required purposes, or may comprise a general purpose computer or other device selectively activated or reconfigured by a computer program stored in the computer. Various general purpose charged particle beam systems may be used with programs in accordance with the teachings herein. Alternatively, the construction of more specialized apparatus to perform the required method steps may be appropriate.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer or controller for a charged particle beam and effectively results in an apparatus that implements the steps of the preferred method.

The invention may also be implemented as hardware modules. More particular, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the system can also be implemented as a combination of hardware and software modules.

Although much of the previous description is directed at semiconductor wafers, the invention could be applied to any suitable substrate or surface. Further, whenever the terms "automatic," "automated," or similar terms are used herein, those terms will be understood to include manual initiation of the automatic or automated process or step. In the following discussion and in the claims, the terms "including" and "comprising" are used in an open-ended fashion, and thus should be interpreted to mean "including, but not limited to . . . "

To the extent that any term is not specially defined in this specification, the intent is that the term is to be given its plain and ordinary meaning. The accompanying drawings are intended to aid in understanding the present invention and, unless otherwise indicated, are not drawn to scale.

The term "integrated circuit" refers to a set of electronic components and their interconnections (internal electrical circuit elements, collectively) that are patterned on the surface of a microchip. The term "semiconductor chip" refers generically to an integrated circuit (IC), which may be integral to a semiconductor wafer, separated from a wafer, or packaged for use on a circuit board. The term "FIB" or "focused ion beam" is used herein to refer to any collimated ion beam, including a beam focused by ion optics and shaped ion beams.

The embodiment above describes a 3D NAND-type structures, but the invention is not limited to such structures and is useful, for example, for DRAMS, and for characterizing trenches and other structures, as well as circular holes.

Some embodiments of the invention provide a method of exposing a region of interest on a work piece using a charged particle beam, comprising: ion beam milling a trench at a first non-normal angle to the work piece top surface to expose a surface adjacent the region of interest and angled with respect to the work piece surface; depositing a protective layer on a portion of the exposed surface adjacent to the region of interest; ion beam milling, at an angle substantially normal to the work piece top surface, a portion of the surface adjacent to the region of interest to expose the region of interest; and observing the region of interest by charged particle beam imaging.

In some embodiments, milling a trench at a first non-normal angle to the work piece top surface includes milling a trench in a region of the work piece having multiple high aspect ratio features.

In some embodiments, the multiple high aspect ratio features are holes.

In some embodiments, depositing a protective layer on a portion of the surface adjacent to the region of interest includes covering steps creating by milling the trench through the high aspect ratio holes.

In some embodiments, performing a subsequent milling step substantially normal to the work piece top surface to expose a second surface of the region of interest and viewing second surface using charged particle beam imaging.

Some embodiments further comprise performing multiple subsequent milling steps to sequentially expose different surfaces of the region of interest and viewing each of the different surfaces using charged particle beam imaging.

In some embodiments, milling a trench at a first non-normal angle to the work piece top surface includes milling a trench having a wall at an angle of between 5° and 50° from a normal to the work piece surface.

In some embodiments, milling a trench includes milling a trench having a wall at an angle of about 18° to about 22° from a normal to the work piece surface.

In some embodiments, depositing a protective layer on a portion of the surface adjacent to the region of interest includes using beam-induced deposition.

In some embodiments, using beam-induced deposition comprises electron-beam induced deposition using electrons having energies greater than 10 keV or greater than 20 keV.

In some embodiments, depositing a protective layer on a portion of the surface adjacent to the region of interest comprises depositing using a protective layer using laser-induced deposition or ion beam induced deposition.

In some embodiments, the region of interest includes a portion of a 3D NAND structure or 3D DRAM structures.

In some embodiments, include a method of creating a cross section of a portion of a high aspect ratio structure for observation, comprising:

milling using a focused ion beam a trench at a non-normal angle to the surface of the sample and at a non-normal angle to the long axis of the high aspect ratio feature;

depositing a protective layer on the wall of the trench at a selected depth of the high aspect ratio feature;

milling using the charged particle beam a cross section through the protective layer and substantially parallel to the surface of the sample to expose a cross section of the high aspect ratio feature; and observing the exposed cross section.

In some embodiments, observing the exposed cross section includes scanning electron microscopy, x-ray analysis, micro-Raman, or other methods.

In some embodiments, milling a second cross section through the protective layer parallel to the first cross section to expose a second cross section of the region of interest.

Some embodiments further comprising sequentially milling using the charged particle beam a cross section through the protective layer and observing the exposed cross section using an electron beam to form a series cross sectional images of a feature in the region of interest.

In some embodiments, depositing a protective layer on the wall of the trench comprises depositing a protective layer using beam-induced deposition.

Some embodiments of the invention provide a method of analyzing a region of interest below a first surface of a work piece, comprising:

directing an ion beam toward the work piece to remove material between the first surface of the work piece and a region of interest to produce a second surface, a portion of the second surface being between the region of interest and the position of the first surface;

depositing a protective layer to the second surface;

directing the ion beam to mill through the protective layer to produce a third surface for analysis, the third surface passing through the region of interest; and observing the region of interest by charged particle beam imaging, the protective layer on the second surface being sufficiently close the feature of interest so that the region of interest is exposed for observation without curtaining.

In some embodiments, the third surface is substantially orthogonal to the first surface.

In some embodiments, the second surface is tilted with respect to a normal to the first surface at an angle between 5° and 50°.

In some embodiments, the second surface is tilted with respect to a normal to the first surface at an angle between about 18° to about 22°.

Some embodiments of the invention provide a system for observing a cross section of a sample, comprising:

an ion optical column for providing a focused beam of ions;

an electron optical column for providing a focused beam of electrons;

a particle detector for detecting secondary particles emitted from the sample;

a controller communicating to a computer memory, the computer memory storing instructions for:

milling a trench at a first non-normal angle to the work piece surface to expose a surface adjacent the region of interest and angled with respect to the work piece surface;

depositing a protective layer on a portion of the surface adjacent to the region of interest;

milling a portion of the surface adjacent to the region of interest to expose the region of interest; and observing the region of interest by charged particle beam imaging.

In some embodiments, the computer memory stores instructions for causing the electron beam to provide electrons having energies greater than 20 keV to deposit the protective layer by electron-beam0-induced deposition.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of exposing a region of interest on a work piece using a charged particle beam, comprising:

ion beam milling a trench at an oblique first angle to a top first surface of the work piece to expose a second surface adjacent to the region of interest that forms an oblique second angle with the first surface;

depositing a protective layer on a portion of the second surface;

exposing a cross section of the region of interest below the protective layer by ion beam milling through the protective layer and the portion of the second surface at a third angle substantially normal to the first surface; and observing the region of interest by charged particle beam imaging the cross section.

2. The method of claim 1 in which milling a trench at a non-normal first angle to the first surface includes milling a trench in a region of the work piece having multiple high aspect ratio features.

3. The method of claim 2 in which the multiple high aspect ratio features are holes.

4. The method of claim 3 in which depositing a protective layer on a portion of the second surface of interest includes milling the trench through the high aspect ratio holes and covering the holes with the protective layer.

5. The method of claim 1 further comprising performing a subsequent milling step substantially normal to the first surface to expose a second cross section of the region of interest and viewing the second cross section using charged particle beam imaging.

6. The method of claim 1 further comprising performing multiple subsequent milling steps to sequentially expose additional cross sections of the region of interest and viewing each of the additional cross sections using charged particle beam imaging.

7. The method of claim 1 in which a wall of the trench comprises the second surface and forms a fourth angle of between 5° and 50° with a normal to the first surface.

8. The method of claim 7 in which the fourth angle is in a range of from about 18° to about 22°.

9. The method of claim 1 in which depositing a protective layer on a portion of the second surface includes using beam-induced deposition.

10. The method of claim 9 in which using beam-induced deposition comprises electron-beam induced deposition using electrons having energies greater than 10 keV.

11. The method of claim 10 in which using electron beam-induced deposition comprises electron-beam induced deposition using electrons having energies greater than 20 keV.

12. The method of claim 1 in which depositing a protective layer on a portion of the second surface comprises depositing using a protective layer using laser-induced deposition or ion beam induced deposition.

13. The method of claim 1 in which the region of interest includes a portion of a 3D NAND structure or 3D DRAM structures.

14. A method of exposing a cross section of a portion of a high aspect ratio feature of a sample for observation, comprising:
    milling using a focused ion beam a trench at a non-normal angle to a first surface of the sample and at a non-normal angle to the long axis of the high aspect ratio feature to expose a planar second surface that is oblique to the first surface;
    depositing a protective layer on the planar second surface at a selected depth of the high aspect ratio feature;
    milling, using the focused ion beam, a cross section through the protective layer and substantially normal to the first surface to expose a cross section of the high aspect ratio feature; and
    observing the exposed cross section.

15. The method of claim 14 in which observing the exposed cross section includes scanning electron microscopy, x-ray analysis, or micro-Raman methods.

16. The method of claim 14 further comprising milling a second cross section through the protective layer parallel to the first cross section to expose a second cross section of the high aspect ratio feature.

17. The method of claim 14 further comprising sequentially milling using the focused ion beam a cross section through the protective layer and observing the exposed cross section using an electron beam to form a series of cross sectional images of the high aspect ratio feature.

18. The method of claim 14 in which depositing a protective layer comprises using electron beam-induced deposition with electrons having energies greater than 15 keV.

19. The method of claim 14 in which depositing a protective layer on the face comprises depositing a protective layer on the face using beam-induced deposition.

20. A method of analyzing a region of interest below a first surface of a work piece, comprising:
    directing an ion beam toward the work piece to remove material between the first surface of the work piece and a region of interest to produce a planar second surface that is oblique to the first surface, a portion of the second surface being between the region of interest and the position of the first surface;
    depositing a protective layer onto the second surface;
    directing the ion beam to mill through the protective layer to produce a third surface for analysis, the third surface passing through the region of interest; and
    observing the region of interest by charged particle beam imaging, the protective layer on the second surface being sufficiently close to the region of interest so that the region of interest is exposed for observation without curtaining.

21. The method of claim 20 in which the third surface is substantially orthogonal to the first surface.

22. The method of claim 21 in which the second surface is tilted with respect to a normal to the first surface at an angle between 5° and 50°.

23. The method of claim 22 in which the second surface is tilted with respect to a normal to the first surface at an angle between about 18° to about 22°.

24. A system for observing a cross section of a region of interest in a sample, comprising:
    an ion optical column for providing a focused beam of ions;
    an electron optical column for providing a focused beam of electrons;
    a particle detector for detecting secondary particles emitted from the sample; and
    a controller communicating to a computer memory, the computer memory storing instructions for:
        milling a trench into an outer first surface of the sample to expose a planar second surface that is adjacent to the region of interest and oblique to the first surface;
        depositing a protective layer on a portion of the second surface adjacent to the region of interest;
        milling a portion of the second surface through the protective layer adjacent to the region of interest to expose the region of interest; and
        observing the region of interest by charged particle beam imaging.

25. The system of claim 24 in which the computer memory stores instructions for causing the electron beam to provide electrons having energies greater than 20 keV to deposit the protective layer by electron-beam-induced deposition.

* * * * *